United States Patent [19]
Wolfman et al.

[11] Patent Number: 5,254,858
[45] Date of Patent: Oct. 19, 1993

[54] SYSTEM HAVING NON-IMAGING CONCENTRATORS FOR PERFORMING IR TRANSMISSION SPECTROSCOPY

[75] Inventors: Dan Wolfman, Tel-Aviv; Aharon Bornstein, Holon, both of Israel

[73] Assignee: State of Israel, Atomic Energy Commission, Sorea Nuclear Research Center, Israel

[21] Appl. No.: 938,008

[22] Filed: Aug. 28, 1992

[30] Foreign Application Priority Data
Sep. 2, 1991 [IL] Israel ......................................... 99367

[51] Int. Cl.$^5$ ............................................. G01N 21/35
[52] U.S. Cl. ................................... 250/339; 250/353; 250/349; 250/504 R
[58] Field of Search .................... 250/504 R, 339, 341, 250/353, 349

[56] References Cited

U.S. PATENT DOCUMENTS

| | | | |
|---|---|---|---|
| 3,370,502 | 2/1968 | Wilks, Jr. ................................. | 88/14 |
| 3,413,468 | 11/1968 | Astheimer ........................... | 250/353 |
| 3,448,276 | 6/1969 | Witte .................................... | 250/353 |
| 3,699,339 | 10/1972 | Taczak et al. ....................... | 250/353 |
| 4,710,630 | 12/1987 | Kuppenheimer, Jr. et al. ... | 250/349 |

OTHER PUBLICATIONS

W. T. Welford and R. Winston, "The Optics of Nonimaging Concentrators: Light and Solar Energy", Academic Press, pp. 148 and 149.

*Primary Examiner*—Carolyn E. Fields
*Attorney, Agent, or Firm*—Leonard Bloom

[57] ABSTRACT

A system for performing IR spectroscopy, including a light source for transmitting a beam of light through a sample on to a detector, including a pair of first conical non-imaging concentrators tapered towards each other and disposed between the light source and the sample, so as to render the beam of light substantially uniform with respect to the sample regardless of their mutual spatial disposition.

4 Claims, 2 Drawing Sheets

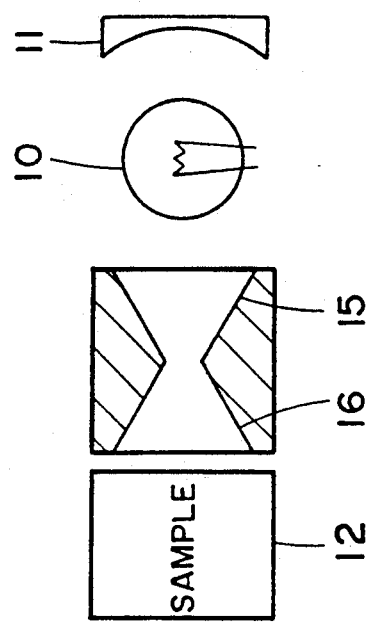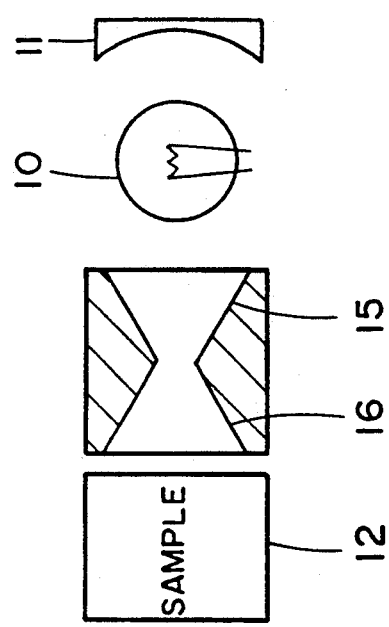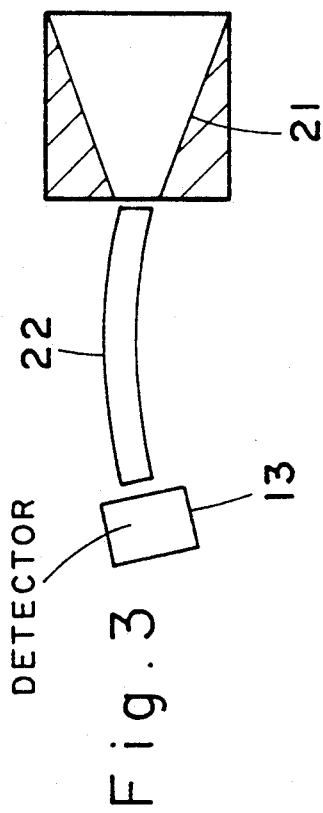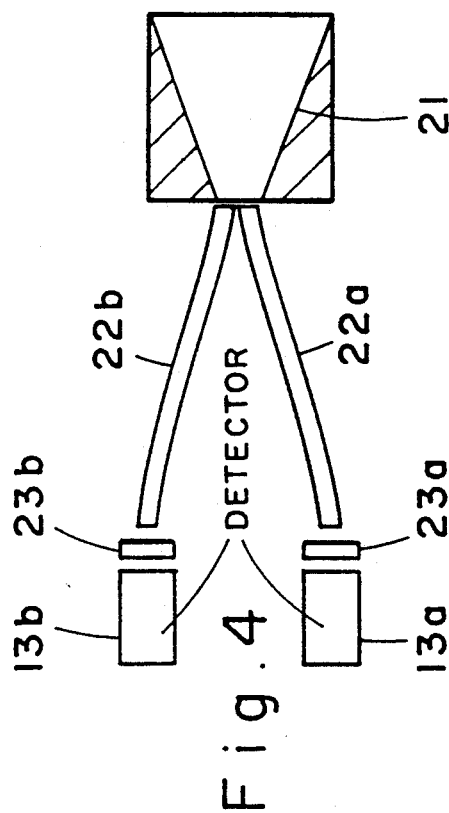

SYSTEM HAVING NON-IMAGING CONCENTRATORS FOR PERFORMING IR TRANSMISSION SPECTROSCOPY

FIELD OF THE INVENTION

This invention is related to IR spectroscopy.

BACKGROUND OF THE INVENTION

Infra red (IR) spectroscopy is used to perform qualitative and quantitative analysis of materials based on the transmission of a light beam through a sample such that different frequency components of the light beam are absorbed by different components of the sample, whereby a frequency analysis of the light emerging from the sample permits analysis of the sample itself.

At its most basic, a spectrophotometer comprises at least the following components: a light source for producing a beam of light, a sample positioned in the path of the light beam and a detector. Since, in practice, the light source is not a point source but, rather, emanates over a relatively broad area, the light beam has a non-uniform cross-section. Consequently, the light passing through a particular portion of the sample depends on the position of the light source relative to the sample and any relative movement therebetween produces different results.

A further consideration which can lead to erroneous results relates to the uniformity of the sample itself. Since this, too, may be non-uniform, even if an ideal light source were employed having a completely uniform cross-section, the detector on the far side of the sample may sense a portion of the light which is not representative of the complete sample owing to the non-uniformity of the sample itself.

These problems may, to some extent, be solved by inserting a diffuser in the light path, but this results also in a loss of light energy and a smaller detector signal.

SUMMARY OF THE INVENTION

It is an object of the invention to provide a system for performing IR spectroscopy in which the effect of a non-uniform light source is significantly reduced and wherein, moreover, the drawbacks associated with a non-uniformly distributed sample are also greatly reduced or eliminated.

According to a broad aspect of the invention, there is provided in a system for performing IR spectroscopy, including a light source for transmitting a beam of light through a sample on to a detector, the improvement wherein there is further included a pair of first conical non-imaging concentrators tapered towards each other and disposed between the light source and the sample, so as to render the beam of light substantially uniform with respect to the sample regardless of their mutual spatial disposition.

The use of non-imaging concentrators in spectroscopy is known per se. Thus, U.S. Pat. No. 3,370,502 (Wilks, Jr.) discloses an absorption cell having a rod with a cell surrounding the rod, radiant energy being directed at one end of the rod and passing down the rod with frustrated multiple internal reflection.

The rod is provided with conical end faces angularly disposed relative to the axis of the rod, whereby rays strike the face at an angle of incidence which is greater than the critical angle and strike the side walls of the rod at less than the critical angle. By this means, incoming rays which are directed on to an end surface of the rod substantially at right angles thereto, are internally reflected along the longitudinal axis of the rod via total internal reflection.

In order to ensure that the rays strike the conical end faces of the rod at the required angle of incidence, a cone whose inner surface is reflective is used to direct the incoming rays to the conical end of the rod at an angle substantially normal thereto. Likewise, a similar reflective cone is employed at an opposite end of the rod, so that rays emerging therefrom strike the internal reflective coating of the cone and are thus reflected substantially parallel to the longitudinal axis of the rod.

The construction proposed by Wilks, Jr. thus requires a specially constructed glass rod, whose end faces are conically shaped. This, of course, requires special polishing techniques which renders expensive the resultant absorption cell.

Furthermore, the arrangement proposed by Wilks, Jr. does not compensate for any inherent non-uniformity in the light source relative to the sampled material.

The physics of non-imaging concentrators is well discussed in the literature. One of the most definitive texts is "The Optics of Nonimaging Concentrators: Light and Solar Energy" by W. T. Welford and R. Winston (Academic Press, Inc.). It is known that non-imaging concentrators have the general form of a cone having rotational symmetry about its longitudinal axis and whose surface may be straight or curved in accordance with design considerations. The internal surface of the non-imaging concentrator should be as reflective as possible within the desired spectral range.

Light entering through the large diameter end is concentrated so that the angle at which light emerges from the non-imaging concentrator is steeper than the angle of entry. When the orientation of the non-imaging concentrator is reversed and light enters through the narrow end, the phenomenon is likewise reversed.

Typical prior art systems for performing ATR spectroscopy employ mirrors or lenses for directing light through the assayed sample and then to the detector. In contrast to this, non-imaging concentrators mix all of the incoming rays and thus maximize the uniformity if the image. Specifically, when the rays reach the detector they represent a true average picture of the sample.

BRIEF DESCRIPTION OF THE DRAWINGS

In order to understand the invention and to see how the same may be carried out in practice, several preferred embodiments will now be described, by way of non-limiting example only, with reference to the accompanying drawings, in which:

FIG. 3 is a schematic representation of a third embodiment according to the invention; and FIG. 4 is a schematic representation of a fourth embodiment according to the invention.

DETAILED DESCRIPTION OF PREFERRED EMBODIMENTS

Figure 1:
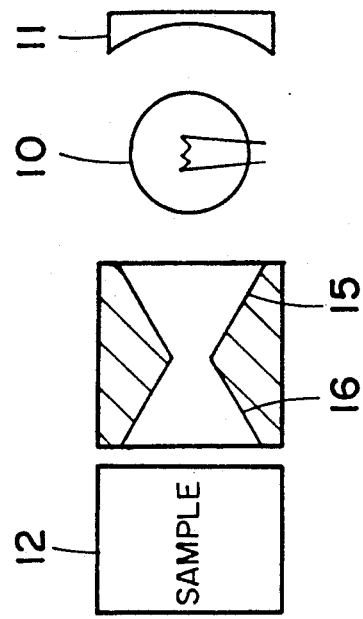
FIG. 1 is a schematic representation of a first embodiment according to the invention.

Referring to FIG. 1, there is shown a light source depicted generally as 10 associated with a reflector 11 for directing a light beam (not shown) through a sample 12 such that light emerging from the sample 12 is directed on to a detector 13.

Disposed between the light source 10 and the sample 12 is a pair of conical non-imaging concentrators (constituting a pair of first conical non-imaging concentrators) 15 and 16 tapered towards each other so that their respective narrow ends are contiguous. The non-imaging concentrator 15 closer to the light source 10 thus concentrates the light beam emerging from the light source 10 so that the concentrated light beam enters the narrow aperture of the non-imaging concentrator 16 closer to the sample 12. Consequently, the light emerging from the non-imaging concentrator 16 is effectively diffused although it suffers from negligible light loss as would be the case with a conventional diffuser.

The light beam thus incident on the sample 12 is substantially uniform with respect thereto, regardless of the actual spatial disposition of the light source 10 relative to the sample 12. Consequently, the light emerging from the sample 12 and incident on the detector 13 depends only on the sample 12 and the resulting analysis is more accurate.

Other preferred embodiments of the invention will now be described with reference to FIGS. 2 to 4 of the drawings. To the extent that FIGS. 2 to 4 contain identical elements to those already described above with reference to FIG. 1, like reference numerals will also be employed.

Figure 2:
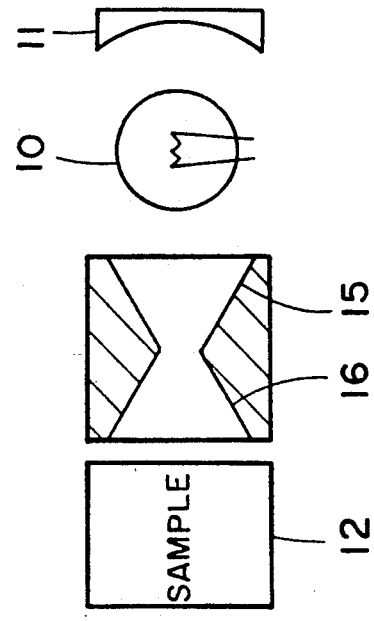
FIG. 2 is a schematic representation of a second embodiment according to the invention.
Figure 2:
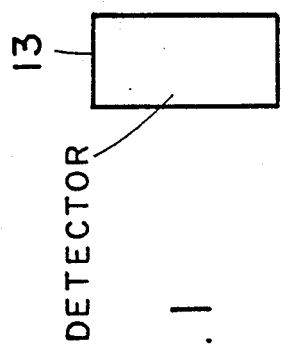
Figure 2:
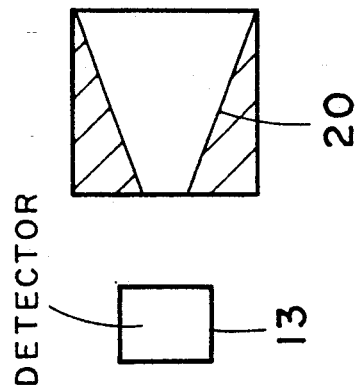

Thus, FIG. 2 shows a light source 10 for directing a beam of light through a sample 12 and on to a detector 13. In this case, a non-imaging concentrator 20 is disposed between the sample 12 and the detector 13 tapered towards the detector 13. By this means, light emerging from the sample 12 is averaged by the non-imaging concentrator 20 prior to its striking the detector 13.

In FIG. 3, a non-imaging concentrator 21 is likewise disposed between the sample 12 and the detector 13, tapered towards the detector 13, but in this case an optical fiber 22 is disposed between the narrow aperture of the non-imaging concentrator 21 and the detector 13. The optical fiber 22 directs the light emerging from the narrow aperture of the non-imaging concentrator 21 to the detector 13.

Finally, FIG. 4 relates to the use of a plurality of detectors of which two are shown, 13a and 13b, and light emerging from a non-imaging concentrator 21 (as shown in FIG. 3) is directed along respective optical fibers 22a and 22b through respective filters 23a and 23b on to the corresponding detectors 13a and 13b.

In such an arrangement, the filters 23a and 23b allow only light of a characteristic wavelength to pass therethrough, whereby the detectors 13a and 13b are responsive to different wavelengths of light determined by the characteristics of the respective filters 23a and 23b.

Whilst the arrangements shown in FIGS. 2 to 4 of the drawings do not include the back-to-back arrangement of the non-imaging concentrators shown in FIG. 1, it will clearly be understood that such an arrangement may equally well be employed in any of the embodiments shown in FIGS. 2 to 4 of the drawings.

We claim:

1. In a system for performing IR spectroscopy, including a light source for transmitting a beam of light through a sample on to a detector, the improvement wherein there is further included a pair of first conical non-imaging concentrators tapered towards each other and disposed between the light source and the sample, so as to render the beam of light substantially uniform with respect to the sample regardless of their mutual spatial disposition.

2. The improvement according to claim 1, wherein there is further included a second conical non-imaging concentrator disposed between the sample and the detector and tapered towards the detector for averaging the beam of light emerging from the sample prior to its striking the detector.

3. The improvement according to claim 2, further including at least one optical fiber disposed between the second conical non-imaging concentrator and the detector for directing the beam of light emerging from the second conical non-imaging concentrator on to the detector.

4. The improvement according to claim 3, including:
a plurality of optical fibers disposed between the second conical non-imaging concentrator and the detector,
a like plurality of filters each disposed at an end of a corresponding one of the optical fibers, and
a like plurality of detectors each disposed at an end of a corresponding one of the optical fibers;
whereby each detector is responsive to a different wavelength of light characteristic of the respective filter.

* * * * *